(12) United States Patent
Mahan et al.

(10) Patent No.: US 6,586,259 B1
(45) Date of Patent: Jul. 1, 2003

(54) PLATELET/LEUKOCYTE INTERACTION ASSAY AND REAGENT THEREFOR

(75) Inventors: Donald E. Mahan, Raleigh, NC (US); Michael W. Stewart, St. Albert (CA)

(73) Assignee: Pharmanetics Incorporated, Morrisville, NC (US)

( * ) Notice: Subject to any disclaimer, the term of this patent is extended or adjusted under 35 U.S.C. 154(b) by 0 days.

(21) Appl. No.: 09/712,165

(22) Filed: Nov. 15, 2000

Related U.S. Application Data
(60) Provisional application No. 60/165,462, filed on Nov. 15, 1999.

(51) Int. Cl.$^7$ ............................................. G01N 33/543
(52) U.S. Cl. ....................... 436/518; 436/523; 436/524; 436/525; 436/526; 436/823; 435/7.1; 435/7.21; 435/7.92; 435/7.24
(58) Field of Search ......................... 436/518, 523–526, 436/501, 533, 823; 435/7.1, 7.21, 7.92, 69, 7.24, 971

(56) References Cited

U.S. PATENT DOCUMENTS

| | | | | |
|---|---|---|---|---|
| 4,115,535 A | * | 9/1978 | Giaever et al. | 436/526 |
| 5,110,727 A | * | 5/1992 | Oberhardt et al. | 435/13 |
| 5,145,784 A | * | 9/1992 | Cox et al. | 436/526 |
| 5,340,719 A | * | 8/1994 | Hajek et al. | 435/7.21 |
| 5,427,913 A | * | 6/1995 | Shaw et al. | 435/7.21 |
| 5,503,982 A | * | 4/1996 | Hendricks et al. | 435/7.21 |
| 5,670,329 A | * | 9/1997 | Oberhardt et al. | 435/13 |
| 5,677,133 A | * | 10/1997 | Oberhardt et al. | 435/7.1 |
| 5,763,199 A | * | 6/1998 | Coller et al. | 435/7.21 |
| 5,952,184 A | * | 9/1999 | Shaw et al. | 435/7.21 |

FOREIGN PATENT DOCUMENTS

| | | | |
|---|---|---|---|
| GB | WO 93/16383 | * | 8/1993 |
| GB | 0625267 | * | 11/1998 |

OTHER PUBLICATIONS

Stuard, et al., "Platelet–neutrophil interactions during hemodialysis: a proposed biocompatibility approach" The International Journal of Artificial Organs, vol. 21, No. 2, 1998, pp. 75–82.

Peyton, et al., "Patients with venous stasis ulceration have increased monocyte–platelet aggregation" Journal of Vascular Surgery, Jun. 1998, vol. 27, No. 6, pp. 1109–1115.

Rinder, et al., "Activated and Unactivated Platelet Adhesion to Monocytes and Neutrophils" The American Society of Hematology, Oct. 1, 1991, Blood, vol. 78, No. 7, pp. 1760–1769.

Lorenzet, et al., "Cell–cell interaction and tissue factor expression" Blood Coagulation and Fibrinolysis, vol. 9, Suppl 1, 1998, pp. S49–S59.

Vorchheimer, et al., "Platelet Glycoprotein IIb/IIIa Receptor Antagonists in Cardiovascular Disease" JAMA, Apr. 21, 1999, vol. 281, No. 15, pp. 1407–1414.

Mannaioni, et al., "Platelets and inflammation: Role of Platelet–derived growth factor, adhesion molecules and histamine" Platelets and inflammation, vol. 46, 1997, pp. 4–18.

Michelson, et al., "Laboratory markers of platelet activation and their clinical significance", Current Opinion in Hematology 1999, pp. 6: 342–348.

Stone, et al., "Conditions under which immobilized platelets activate as well capture flowing neutrophils", Blackwell Science Ltd. British Journal of Haematology, 1999, 105: 514–522.

Gawaz, et al., "Platelet–Leukocyte Aggregates During Hemodialysis: Effect of Membrane Type" Artificial Organs, vol. 23, No. 1, 1999, pp. 29–36.

Gawaz, et al., "Platelet activation and interaction with leucocytes in patients with sepsis or multiple organ failure", 1995 Blackwell Science Ltd., European Science Journal of Clinical Invesigation, 25, pp. 843–851.

Rinder, et al., "Selective blockade of membrane attack complex formation during simulated extracorporeal circulation inhibits platelet but not leukocyte activation", The Journal of Toracic and Cardiovascular Surgery, vol. 118, No. 3, Sep. 1999, pp. 460–466.

Weber, et al., "Neutrophil Accumulation on Activated, Surface–adherent Platelets in Flow is Mediated by interaction of Mac–1 with Fibrinogen Bound to βIIbγ3 and Stimulated by Platelet–activating Factor", The American Society for Clinical Investigation, Inc. vol. 100, No. 8, Oct. 1997, pp. 2085–2093.

\* cited by examiner

Primary Examiner—Long V. Le
Assistant Examiner—Gary Counts
(74) Attorney, Agent, or Firm—Oblon, Spivak, McClelland, Maier & Neustadt, P.C.

(57) ABSTRACT

A platelet/leukocyte interaction assay method and reagent therefor are provided using the presence of a solid-phase stimulus, such as magnetic or non-magnetic particles or mixtures thereof, having bound to the surface thereof one or more ligands that interact directly with platelets, leukocytes or both, for providing a fast, reliable point-of-care assessment of platelet/leukocyte interaction.

26 Claims, 4 Drawing Sheets

Stroke/TIA Patients-Platelet/Leukocyte Interaction

| Patient | Platelets | | | Monocytes | | | Granulocytes | | |
|---|---|---|---|---|---|---|---|---|---|
| | Pre | Post | %RPC | Pre | Post | %drop | Pre | Post | %drop |
| 1 | 183 | 25 | 14 | 0.4 | 0.4 | 0 | 8.6 | 3.1 | 64 |
| 2 | 141 | 41 | 29 | 0.3 | 0.3 | 0 | 6.2 | 5.8 | 6 |
| 3 | 151 | 2 | 1 | 0.4 | 0.2 | 50 | 2.6 | 2.4 | 8 |
| 4 | 123 | 17 | 14 | 0.2 | 0.3 | -50 | 5.1 | 5 | 2 |
| 5 | 148 | 9 | 6 | 0.2 | 0.3 | -50 | 1.5 | 3 | -100 |
| 6 | 239 | 10 | 4 | 0.3 | 0.3 | 0 | 3.6 | 3.7 | -3 |
| 7 | 204 | 32 | 16 | 0.2 | 0.3 | -50 | 5.8 | 5.5 | 5 |
| 8 | 156 | 4 | 3 | 0.3 | 0.3 | 0 | 4.6 | 3.5 | 24 |
| 9 | 205 | 14 | 7 | 0.4 | 0.1 | 75 | 4.8 | 3.8 | 21 |
| 10 | 134 | 14 | 10 | 0.4 | 0.2 | 50 | 2.9 | 3.2 | -10 |
| 11 | 192 | 4 | 2 | 0.4 | 0.1 | 75 | 2.8 | 1.3 | 54 |
| 12 | 172 | 3 | 2 | 0.3 | 0.2 | 33 | 5.2 | 4.7 | 10 |
| 13 | 269 | 11 | 4 | 0.6 | 0.3 | 50 | 4.2 | 2.9 | 31 |
| 14 | 82 | 20 | 24 | 0.3 | 0.3 | 0 | 2.1 | 1.85 | 12 |
| 15 | 203 | 117 | 58 | 0.5 | 0.7 | -40 | 4.2 | 3.55 | 15 |
| 16 | 164 | 96 | 59 | 0.4 | 0.45 | -13 | 5.9 | 4.85 | 18 |
| 17 | 184 | 105 | 57 | 0.5 | 0.55 | -10 | 5.7 | 5.95 | -4 |
| 18 | 244 | 61 | 25 | 0.2 | 0.5 | -150 | 5.1 | 6.05 | -19 |
| 19 | 150 | 24 | 16 | 0.3 | 0.6 | -100 | 6.2 | 6.5 | -5 |
| 20 | 145 | 39 | 27 | 0.4 | 0.2 | 50 | 3 | 2.95 | 2 |

|  | Mean | 18.9 | #>9 | 7 | #>9 | 9 |
|---|---|---|---|---|---|---|
|  | SD | 18.93 | | | | |
|  | #<30 | 17 | | | | |
|  | #>30 | 3 | | | | |

\* 17 OF 20 Stroke/TIA patients tested demonstrated residual platelet counts less than 30%.
\* 7 of 20 Stroke/TIA patients tested showed a decrease in monocyte counts after reacting the whole blood with VWF-coated beads
\* 8 of 20 Stroke/TIA patients tested showed a decrease in granulocyte counts after reacting the whole blood with VWF-coated beads.
\* 12 of 20 Stroke/TIA patients tested showed a decrease in monocyte or granulocyte counts after reacting the whole blood with VWF-coated beads.
\*\* Of 63 control samples tested, 5 samples demonstrated a decrease in the monocyte counts after reacting the whole blood with the VWF-coated beads.
\*\* Of 63 control samples tested, 12 samples demonstrated a decrease in the granulocyte counts after reacting with the VWF-coated beads.
\*\* Of 63 control samples tested, 13 samples showed a decrease in either monocyte or granulocyte counts after reacting with the VWF-coated beads.
\*\* Of the 13 control samples showing a decrease in either monocyte or granulocyte counts after reacting with the VWF-coated beads, 8 samples exhibited residual platelet counts of less than 30%.

PLATELET/LEUKOCYTE INTERACTION ASSAY AND REAGENT THEREFOR

This application claims priority of provisional application Ser. No. 60/165,462, filed Nov. 15, 1999.

BACKGROUND OF THE INVENTION

1. Field of the Invention

The present invention relates to a platelet/leukocyte interaction assay allowing for point of care assessment of interaction of platelets and leukocytes, and the reagents therefor.

2. Discussion of the Background

Platelets are known to interact with leukocytes both as a consequence of contact during normal blood flow (Stone and Nash, British Journal of Haematology, 105:514–22, 1999; Lorenz et al, Blood Coagulation and Fibrinolysis, 9:S49–59, 1998) and as a consequence of various pathological processes (Rinder et al, Journal of Cardiovascular Surgery, 118:460–6, 1999; Pevton et al, Journal of Vascular Surgery, 27:1109–15, 1998; Stuard et al, International Journal of Artificial Organs, 21:75–82, 1998; Gawaz et al, European Journal of Clinical Investigation, 25:843–51, 1995).

Pathological conditions such as Unstable Angina, Coronary Artery Disease (CAD), and Stroke are characterized by high levels of platelet and leukocyte activity. Measurement of platelet/leukocyte interaction can be predictive of these pathological states, particularly in combination with other diagnostic factors. Also, measurement of platelet/leukocyte interaction can be used as a means of monitoring therapy directed toward altering platelet and/or leukocyte function.

Exposure of flowing blood to artificial surfaces has been shown to enhance platelet/leukocyte interaction. The cell types involved and the extent of the interaction vary with the composition of the artificial surface in contact with the blood (Gawaz et al, Artificial Organs, 23:29–36, 1999).

Although platelet/leukocyte interactions have been quantified using various techniques (Hendricks et al, U.S. Pat. No. 5,503,982; Rinder et al, Blood, 78:1760, 1991;), assessment of the interaction has relied upon measurement of circulating platelet/leukocyte complexes. Measurements, to date, have taken the form of evaluating pre-existing platelet/leukocyte interactions in a blood sample.

In some pathological conditions (e.g. Acute Myocardial Infarction, AMI; post Angioplasty, PTCA; etc.) platelet/leukocyte complex formation is associated with interaction with damaged subendothelium, whether directly (plaque formation) or indirectly (release of biochemical markers such as ICAM-1, see Hendricks et al, U.S. Pat. No. 5,503, 982).

Current assay systems used to assess platelet/leukocyte interactions, as exemplified by Hendricks et al (U.S. Pat. No. 5,503,982), evaluate pre-existing (circulating) platelet/leukocyte complexes and do not utilize a component representative of the vessel subendothelium (i.e. extracellular matrix) or other solid-phase stimulus. Moreover, the threshold at which discrete platelets and leukocytes interact could vary depending on the activation status of these cells at the time of testing. It is known in the art that platelet and/or leukocyte activation is a necessary prerequisite of platelet/leukocyte binding. It is also known in the art that certain pathological conditions are associated with upregulation of platelet and/or leukocyte activity. However, the upregulation in cellular activity associated with the pathological process may be insufficient to support platelet/leukocyte complex formation without additional stimulation and moreover, may not be detectable using conventional systems, which lack a stabilizing solid-phase support upon which the platelet/leukocyte complex could be maintained. (A solid-phase stimulus could be used as a means of localizing pre-existing platelet leukocyte complexes and/or inducing complex formation and localization in cells predisposed to do so.)

It is desirable that assay systems designed to incorporate the use of a solid-phase component such as immobilized subendothelial/extracellular matrix be facile, rapid and of reasonable cost to be useful in detecting platelet/leukocyte interaction in a clinical setting.

The present invention addresses shortcomings of previous methods and technologies by using microparticles of various compositions coated with plasma proteins and/or extracellular matrix proteins, either singly or in combination, to facilitate rapid assessment of platelet/leukocyte binding.

Platelets can interact with leukocytes through various mechanisms, such as contact during normal blood flow (Lorenz et al, Blood Coagulation and Fibrinolysis, 9:S49–S59, 1998), or as a consequence of a pathological process associated with platelet hyperactivity (Spanygenberg, Thrombosis Research, 74:S35–S44, 1994; Rinder et al, Journal of Cardiovascular Surgery, 118:460–6, 1999) or due to an inflammatory process (Gawaz et al, European Journal of Clinical Investigation, 25:843–51, 1995). Receptors found on the platelet surface interact with receptors found on various leukocytes through direct bridging or through an indirect linkage involving intermediary molecules (Weber and Springer, Journal of Clinical Investigation, 100:2085–93, 1997). Upregulation of platelet and/or leukocyte activity favors enhanced platelet/leukocyte interaction (Rinder et al, 1999; Stone and Nash, British Journal of Haematology, 105:514–22, 1999; Konstantopoulos et al, 1998; Gawaz et al, 1995; Spanenberg, 1994).

Individuals with Coronary Artery Disease (CAD), Diabetes or Cerebrovascular Ischemia demonstrate both platelet hyperactivity and an ongoing inflammatory process (Michelson and Furman, Current Opinion in Hematology, 6:342–8, 1999). Treatment of patients with CAD has involved the use of anti-platelet agents and anti-inflammatory medications (Vorchheimer et al, JAMA 281:1407–14, 1999; Mannaioni et al, Inflammation Research, 46:4–18, 1997).

Platelet/monocyte (Hendricks et al, U.S. Pat. No. 5,503, 982) and platelet/neutrophil (Gawaz et al, European Journal of Clinical Investigation, 25:843–51, 1995) interaction have been suggested to be predictive of acute myocardial infarction (AMI) and inflammation, respectively. A corollary to platelet/leukocyte interaction in various pathological conditions is involvement of the vessel wall, whether in plaque formation for example, or a localized inflammatory reaction.

Platelet function assessment using immobilized extracellular matrix proteins has been described by Shaw and Stewart (U.S. Pat. No. 5,427,913). The authors demonstrated that von Willebrand factor (VWF) immobilized on polystyrene beads could be used to activate platelets and thereby determine the functional status of platelets from patients with platelet function defects. In addition, the authors also demonstrated that the effects of agents designed to alter platelet function could be monitored using bead-immobilized VWF as a stimulus. The results of these studies underline the importance of evaluating a normal hematological interaction or the hematologic consequence of a pathological state in the presence of an agent that mimics components of the vessel wall.

Although Shaw and Stewart describe methods and compositions of determining platelet function, there is no description or suggestion of using their method for evaluating platelet/leukocyte interaction.

CVDI's TAS™ analyzer measures the kinetics of fibrin polymerization following activation of the coagulation pathway in a patient's blood sample. The TAS™ analyzer and disposable were designed for use with whole blood in a point-of-care setting. Paramagnetic iron oxide particles (PIOP) are an essential component of the detection system for each of the tests developed for the TAS™ analyzer. The PIOP and other lyophilized ingredients for a particular test are located in the shallow reaction chamber of the TAS test card disposable. In addition to PIOP, the test reagent may contain buffers, stabilizers, fillers and specific coagulation pathway activator or agents. A test is initiated by insertion of a dry-chemistry test card into a slot of the TAS™ analyzer that automatically positions the test card reaction chamber above an electromagnet. This chamber is also illuminated with infrared light from a light emitting diode. The instrument measures reflected infrared light from the surface of the test card by means of a solid state photodiode detector. A test is automatically initiated when the analyzer photodetector measures a change in reflected light intensity when blood or plasma is added to the sample well of the test card and, through capillary action, is pulled into the reaction chamber. The activators present in the reaction chambers stimulate the coagulation cascade in the patient's sample to produce thrombin, which in turn catalyzes the formation of the fibrin clot.

During a clotting test the TAS™ analyzer electromagnet oscillates on and off every second. The magnetic particles stand up when the electromagnet is on, causing more light to be reflected to the detector, and fall down when it is off, causing less light to be detected. This movement of PIOP produces an alternating current (AC) signal from the photodetector. As the test proceeds, more and more fibrin polymerization occurs and the PIOP movement is less. The analyzer in accordance with predetermined algorithms interprets the signal produced by the relative movement of the PIOP and reports an endpoint (clotting time) appropriate for each test.

Although PIOP is an integral component of the TAS™ detection system, it does not participate directly in activation of the coagulation cascade or fibrin polymerization. To prevent undesired interactions between PIOP and activators within the reaction chamber of a test card, the PIOP is coated or blocked with bovine serum albumin (BSA). BSA is a protein commonly used by those skilled in assay development to prevent unwanted interactions between surface components of a test and its active ingredients. The TAS™ system was designed to monitor fibrin polymerization and not interactions between platelets and leukocytes.

SUMMARY OF THE INVENTION

Accordingly, one object of the present invention is to provide an assay for platelet/leukocyte interaction that can be used with a variety of blood products as the sample, including whole blood, with ease of detection.

A further object of the present invention is to provide an assay for platelet/leukocyte interaction that can be used on the TAS™ system for rapid determination of platelet/leukocyte interactions.

A further object of the present invention is to provide a platelet/leukocyte interaction assay reagent, preferably in a dry chemistry test card format that can be used in the assay of the present invention.

A further object of the present invention is to provide a method for diagnosis of conditions resulting in platelet/leukocyte interactions using the assay of the present invention.

A further object of the present invention is to provide a method for determination of platelet and/or leukocyte hyperactivity using the assay of the present invention.

These and other objects of the present invention have been satisfied by the discovery of a method of assessing platelet/leukocyte interaction, comprising:

contacting a whole blood or blood-derived sample with a solid-phase stimulus, wherein said solid-phase stimulus has bound to a surface thereof a ligand selective for binding platelets or leukocytes, and detecting formation of one or more platelet/leukocyte/solid-phase stimulus complexes, and the reagents for performing the method, as well as the use of the method for detection of the occurrence of platelet/leukocyte interaction caused by various disease conditions and the predisposition of subjects to those conditions.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein;

FIG. 3 is a tabular representation of count data obtained in the Examples described below.

DETAILED DESCRIPTION OF THE PREFERRED EMBODIMENTS

The present invention relates to a platelet/leukocyte interaction assay and a reagent for use in the assay. The assay of the present invention monitors interaction between platelets and leukocytes in the blood or blood-derived sample. The assay can be performed either in a wet chemistry format or a dry chemistry format.

Within the context of the present invention, the term "leukocyte" and forms thereof is to be given its normal medical meaning. Leukocytes include, but are not limited to, granulocytes, lymphocytes and monocytes. Within the granulocyte subgroup, there are neutrophils, basophils and eosinophils. The present invention most preferably is used to detect interaction of platelets with granulocytes and monocytes. However, platelet/leukocyte interactions of all types are also within the scope of the present invention assay.

The present invention relates to methods and compositions for evaluating and quantifying platelet/leukocyte interaction in the presence of a solid phase stimulus, in suspension. The solid phase stimulus of the present invention would consist of plasma proteins and/or extracellular matrix proteins, or fragments thereof, in single or in combination immobilized on microparticles. These proteins could be attached to the microparticles passively or through a covalent linkage and/or through bridging molecules. The microparticles may be of a single type or, in certain embodiments, can include two or more differing types of microparticles.

In a preferred embodiment of the invention the proteins used to coat the solid phase support would be chosen from the group of von Willebrand factor, fibrinogen, collagen, fibronectin, vitronectin, thrombospondin, laminin, osteopontin, coagulation factors (in their active or inactive forms), fibrillin, chondroitin sulfate, or heparin sulfate. These proteins or fragments thereof, would be immobilized onto the solid phase support either in single or in combination, either passively or through a covalent linkage. Attachment of the proteins to the solid-phase particulate support could also be accomplished using spacer molecules, as would be readily apparent to those skilled in the art.

The solid phase stimulus would be mixed in suspension with a source of platelets and leukocytes for a given period of time under defined force conditions. The force conditions could be such that a range of reactivities could be possible; from simple contact of the platelet/leukocyte complexes with the solid-phase stimulus to effect binding of the complexes, through to activation of the platelets and/or leukocytes under high force conditions (e.g. high shear or turbulent flow) to induce platelet/leukocyte complex formation on the suspended solid-phase stimulus. The mixing conditions could take the form of stirring, shaking, aspiration, application of electromagnetic fields and/or beams, ultrasound, or the application of shear through the use of an apparatus such as a cone-plate viscometer or flow of the suspension through conduits of predefined dimensions. The conduits could take the form of glass or plastic tubing; channels formed in microchips or blood vessels derived from mammals, or conduits on reaction test cards, such as those described in Oberhardt, U.S. Pat. No. 5,110, 727, hereby incorporated by reference. The assay sample is typically a suspension containing the platelets and leukocytes and is blood or a blood derived sample. The sample can preferably be whole blood from a finger stick, diluted whole blood, anticoagulated whole blood, washed cells, buffy-coat or platelet rich plasma. The platelet/leukocyte suspensions could be obtained either directly from a subject to be tested or from blood products that have been stored for research or transfusion purposes, originally collected from the subject.

In a preferred embodiment of the invention, the subject is a mammal, most preferably a human.

Evaluation of the interaction between the platelets and leukocytes comprises attachment of the cells to the solid-phase support through the application of a predefined set of force conditions, such that either qualitative and/or quantitative analysis of the interaction can be accomplished.

Qualitative analysis can be performed by any method capable of detecting the platelet/leukocyte/solid-phase support complexes formed during the assay. Suitable examples of such methods include, but are not limited to, macroscopic examination (by eye), microscopy, photo-microscopy, electron microscopy (transmission or scanning), confocal microscopy or video microscopy. Qualitative analysis could alternatively (or concomitantly) take the form of histochemical analysis, immuno-histochemical analysis, genetic analysis (PCR, FISH, Southern Blotting) or Western Blotting.

The assay can also be used for quantitative or semi-quantitative determination of the platelet-leukocyte interaction. Such analysis can be performed using any method capable of detecting and counting the number of platelet/leukocyte/solid-phase support complexes present in the assayed sample. Suitable quantitative or semi-quantitative analysis methods include, but are not limited to, cell counting, flow cytometry, static cytometry, laser-scanning cytometry, turbidity measurement, absorbance measurement, colorimetric measurement, enzyme-linked immunosorbent assay (ELISA), radio-immunoassay, immunoradiometric assay, gel exclusion chromatography, affinity chromatography, intra-cellular or extra-cellular ion flux measurement, measurement of cellular releasates, measurement of solid-phase/platelet/leukocyte aggregate size, or latex agglutination assays. Preferred methods for such quantitative determination are cell counting and cytometry (both flow and static). Suitable cytometers include, but are not limited to, the ONCYTE® and LSC® static cytometers available from CompuCyte, the FACSCan® and FACSCalibur® flow cytometers available from Becton Dickinson and the EXCEL® flow cytometer available from Coulter.

Qualitative or quantitative assessment of platelet/leukocyte interaction can be performed in combination with other assays providing the user with information to allow a more definitive identification of a pathological condition and/or the appropriate treatment regimen. As an example an individual may wish to determine platelet function (such as described in Mahan et al, U.S. Provisional Application No. 60/202,638, hereby incorporated by reference; or by a conventional platelet function test), and cardiac marker enzymes in conjunction with assessment of platelet/leukocyte interactions to more clearly define the occurrence of AMI. Such combinations of assays could be constructed to run concurrently or simultaneously on a single device. Other combinations of desirable assays for defined pathological conditions are readily evident to those skilled in the art and should not be limited to those mentioned, herein.

The solid-phase stimulus of the present invention provides a means of localizing platelet/leukocyte conjugates enabling rapid assessment of the degree of platelet/leukocyte interaction. The solid-phase stimulus can also induce platelet and/or leukocyte activation facilitating platelet/leukocyte complex formation on the solid-phase stimulus.

In a preferred embodiment of the invention, the particles are coated with a source of plasma protein(s), or fragments thereof Exemplary plasma proteins include, but are not limited to, von Willebrand factor, fibrinogen, fibronectin, or blood coagulation factors (in their active or inactive, i.e. zymogen forms), such as Factor II, Factor IIa, Factor V, Factor Va, Factor VIII, Factor VIIIa, Factor IX, Factor IXa, Factor X, Factor Xa, Factor XI, Factor XIa, Factor XII, Factor XIIa, Factor XIII, Factor XIIIa, collagen, vitronectin, laminin, osteopontin, fibrillin, chondroitin sulfate, heparin sulfate and combinations thereof.

In a preferred embodiment of the invention the particles are coated with extracellular matrix protein(s), or fragments thereof, in single or in combination. Exemplary extracellular matrix proteins include, but are not limited to, von Willebrand factor, fibronectin, collagen, osteopontin, laminin, thrombospondin, fibrillin, chondroitin sulfate, or heparin sulfate or combinations thereof.

It is also possible to coat some of the particles with a leukocyte binding ligand, such as leukocyte selective antibodies, or proteins or fragments thereof that bind to leukocyte membrane components. Examples of such proteins include VCAM-1, fibronectin, laminin, ICAM-1, ICAM-2, ICAM-3, collagen, osteopontin, vWf, vitronectin, thrombospondin, mucosal addressin cell adhesion molecule 1 (MadCAM-1), P-selectin, L-selectin and E-selectin.

The microparticles to which the proteins are coated to form the solid phase stimulus can be any shape. In particular, they can take the form of microspheres or irregularly shaped microparticles. The microspheres or irregularly-shaped microparticles can be made of any material to which it is capable to bind, either directly or indirectly, one or more of the above-noted proteins or fragments thereof. These microspheres or irregularly-shaped microparticles can be any desired particle size, preferably on the same order of size as the PIOP described below, more preferably having a particle size of from 1 to 20 microns. Preferred examples of materials comprising the microspheres or irregularly-shaped microparticles include, but are not limited to, polystyrene and/or latex, polycarbonate, acrylonitrile, carboxylate, teflon, glass, nylon, dextran, agarose, acrylamide, silica, pollen, micro-organisms (viable or non-viable), iron oxide, paramagnetic iron oxide, paramagnetic particles, non-magnetic metal beads, gold, platinum, or palladium. Most preferred are the polystyrene beads as described by Stewart et al, *British J Haematology*, 97, 321–329 (1997) and Shaw et al, U.S. Pat. No. 5,952,184, each of which are hereby incorporated by reference. The microspheres or irregularly shaped microparticles could also be paramagnetic in nature and/or fluorescently tagged and/or tagged with an enzyme suitable to elicit a light or color reaction in the presence of the appropriate substrate and/or chemicals.

In one preferred embodiment of the invention the microparticles comprise polystyrene, are spherical in nature, and are coated with von Willebrand factor of human origin.

In a most preferred embodiment of the invention, the von Willebrand factor coated microspheres are mixed with whole blood (unanticoagulated or anticoagulated) for a predefined length of time under predefined force conditions, sufficient to capture platelet/leukocyte complexes or to induce platelet/leukocyte complex formation on the von Willebrand factor coated microspheres, following which the existence and/or amount of such complex formation is determined.

In a further preferred embodiment, the assay of the present invention is run using a reagent comprising two central reagent elements. The first is magnetic particles, preferably paramagnetic iron oxide particles (PIOP), such as those currently employed in the TAS™ analyzer (described in U.S. Pat. No. 4,849,340; 5,110,727; 5,350,676; 5,601, 991; 5,670,329; and 5,677,233, each of which is hereby incorporated by reference), which have been modified by binding a ligand to their surface that can either (1) interact directly with the leukocytes or (2) interact with the blood platelets. While a variety of magnetic particles can be used, as described in U.S. Pat. No. 5,110,727, the preferred magnetic particles are PIOP. Accordingly, the following description will refer to PIOP for convenience, but it is to be understood that unless otherwise indicated, the term PIOP can refer to any magnetic particles type. The PIOP, as in the conventional TAS applications, also plays a central role in the assay monitoring and detection system, whereby movement of the modified PIOP in response to a moving magnetic field is monitored to determine the endpoint of the assay.

The second central reagent element in this preferred embodiment is non-magnetic beads or microspheres coated with a ligand that can interact directly with blood platelets. These non-magnetic beads or microspheres can be any desired particle size, preferably on the same order of size as the PIOP, more preferably having a particle size of from 1 to 20 microns. The non-magnetic beads can be made from any non-magnetic material that is capable of having a ligand bound to its surface. Preferred materials for preparation of the non-magnetic beads include, but are not limited to, those listed above for the microspheres or irregularly-shaped particles, such as polystyrene beads, polyolefin beads, glass beads, and even non-magnetic metal beads. Most preferred are the polystyrene beads as described by Stewart et al, *British J. Haematology*, 97, 321–329 (1997) and Shaw et al, U.S. Pat. No. 5,952,184, each of which are hereby incorporated by reference. Other reagents known to those skilled in the art to enhance functional stability, reagent drying and material rehydration on sample addition may also be added to the test formulation, such as anticoagulants, buffers, etc, and as described in the Oberhardt, and Shaw patents described herein.

The ligand can be bound to the particles directly or indirectly through a spacer, so long as the activity of the ligand is not impaired. The direct binding can occur either covalently or non-covalently. Indirect binding can occur through spacers, including but not limited to peptide spacers, antibody spacers or carbohydrate spacers. These spacers normally act only as bridges between the particle and the ligand, but could be used in order to alter the effectiveness of the ligand/receptor interaction. For example, coupling vWf to the particle through a 7 amino acid peptide bridge could decrease the interaction of vWf with the platelet receptor. However, use of the active segment of vWf, coupled to the particle through the same 7 amino acid peptide bridge could result in upregulation of the vWf fragment/receptor interaction. Similar enhancements of other types have been seen by Beer et al, *Blood*, 79, 117–128 (1992).

In one embodiment of the present invention assay, the reagent can contain only the magnetic particles when the oscillating magnetic field is used. However, as described below, when the rotating field is used, a preferred reagent contains both magnetic and non-magnetic particles having ligands bound to both types of particles.

The ligand that interacts with blood platelets on the non-magnetic particles of this embodiment can be any compound capable of performing that function, that results in activation of the platelets. Suitable ligands include, but are not limited to, von Willebrand factor (vWf), collagen and thrombin, as well as fragments (also known as mimetopes, such as those described by Miller, U.S. Pat. No. 5,877,155, hereby incorporated by reference) thereof. Most preferred is the use of von Willebrand factor or a fragment thereof as the ligand.

The ligand used on the non-magnetic particles and the magnetic particles can be the same ligand or different ligands. When the ligand is the same on both types of particles, it is further necessary to provide a leukocyte marker in the reagent. The leukocyte marker can be any conventional marker known to identify the presence of leukocytes, such as flourescent markers. Examples of suitable leukocyte markers include CD45, CD18, CD11a/CD18 (LFA-1), CD11b/CD18 (Mac-1), CD11c/CD18, P-selectin ligand (PSGL-1), and CD34. In the case where the ligand is the same on both types of particles, the ligand is most preferably von Willebrand factor or a fragment thereof. The ligand should be present on the surface of the magnetic and non-magnetic particles in an amount sufficient to provide binding to, and activation of, the platelets, such that a sufficient number of platelets are activated to result in an assay endpoint within a time period of from 1 to 20 minutes, preferably from 2–4 minutes. For example, in the case of the rotating magnetic field as described below, the endpoint is reached when the initially formed rotating PIOP ring collapses into a solid disc or dot.

Alternatively, the ligands bound to the two types of particles can be different. The ligands can both be ligands that interact directly with platelets, while being different from one another. In such case, the same type of leukocyte marker would be needed as noted above. However, in a further embodiment, one ligand can be a ligand that interacts directly (and selectively) with platelets, while the other ligand interacts directly (and selectively) with leukocytes. Examples of such leukocyte selective ligands include leukocyte selective antibodies, VCAM-1, fibronectin, laminin, ICAM-1, ICAM-2, ICAM-3, collagen osteopontin, vWf, vitronectin, thrombospondin, mucosal addressin cell adhesion molecule 1 (MadCAM-1), P-selectin, L-selectin, and E-selectin (all unlabeled or labeled with a fluorescent tag such as FITC or phycoerythrin). In such a case, collapse of the rotating PIOP ring would only occur through formation of the platelet/leukocyte/particles complex, thus signalling the interaction of platelets and leukocytes. While this provides a qualitative determination of platelet/leukocyte interaction, this embodiment can also provide a quantitative determination of the interaction by use of a leukocyte marker such as described above or by comparison and correlation of the collapse time of the PIOP ring with one or more standards having known platelet/leukocyte interaction activities.

In the assay of the present invention, platelet/leukocyte interaction will be observed when there is either platelet hyperactivity or leukocyte hyperactivity. However, when both activities are normal or low, the interaction will not normally be observed. This can be forced to occur, however, by the application of high force conditions to activate the platelets and/or leukocytes, as described above. High force conditions can be used to determine the susceptibility of a subject for platelet/leukocyte interaction and hence can provide a diagnostic tool for determining propensity or predisposition to the various disease states involving such interactions, as noted above, particularly when combined with other diagnostic tools for the specific disease state.

The assay of the present invention can be either in a wet chemistry or dry chemistry format. In either format, the test can be performed on a relatively flat reaction surface, preferably in a reaction slide such as that described in the above-noted Oberhardt U.S. Patents. Most preferably, the assay is performed in a dry chemistry format using a reaction slide or card as described in U.S. Pat. No. 5,110,727, the contents of which are hereby incorporated by reference. The present assay can also be adapted for use in disposables with reagent chambers of any desired size and shape.

To perform a preferred embodiment of the platelet/leukocyte interaction assay of the present invention, it is necessary to place the reaction chamber into an oscillating magnetic field, such as that described by U.S. Pat. No. 5,110,727 (previously incorporated by reference) or into a rotating magnetic field, such as that described in U.S. Pat. No. 5,670,329 (hereby incorporated by reference). Most preferably, the assay is performed in the presence of the rotating magnetic field. The magnet (either oscillating field type or rotating field type) must be designed such that the field can influence substantially all of the PIOP present in the reaction chamber. In the preferred example of the rotating magnetic field, when the reaction chamber is that present in a TAS test card, the separation between the magnetic poles may range from 0.5 to 2.5 cm. The magnet must be positioned sufficiently close to the reaction chamber to cause movement of PIOP when the magnetic field is rotating. The rotating magnetic field can rotate at any frequency capable of sustaining the circular movement of the magnetic particles of the system, with the rotational frequency being preferably from 2,000 to 2,500 rpm. The rotating magnetic field can be provided by the rotation of a permanent magnet about a central axis as described in U.S. Pat. No. 5,670,329, or can be generated by sequential activation of a series of electromagnets in a circular arrangement, as also described in U.S. Pat. No. 5,670,329.

One design for the magnet for providing a rotating magnetic field in the present assay comprises two sets of button magnets mounted on a metal disk approximately 3.4 cm in diameter. The metal disk base is attached at its center to the shaft of a DC electric motor. Each button magnet assembly contains three readily available button magnets of approximately 1 cm in diameter. The button magnets are positioned directly opposite of one another on the metal base. On the top of each button magnet assembly is placed one-half of a second metal disk (semi-circle, half of a circle) approximately 3 mm thick with a radius of 9 mm. The straight edges of the two disks face one another and are separated by approximately 1.5 cm. The entire assembly is positioned approximately 2–4 mm beneath the reaction chamber of a test card.

The assay is initiated by addition of a whole blood or platelet rich plasma sample to a reaction chamber containing the reagents described, positioned above the magnet, preferably generating a rotating magnetic field most preferably at a rotational frequency of 2500 rpm. In the most preferred embodiment using a dry chemistry format, the reagent is re-hydrated by the sample, freeing the magnetic particles and allowing them to begin to move in response to the rotating magnetic field. In the presence of the rotating field, the magnetic particles organize as a ring or band of dark material traveling along the outer edges of the reaction area. The center of the ring initially is clear or slightly gray (i.e. contains substantially fewer PIOP). The non-magnetic particles are preferably chosen so as to be invisible to the detection system.

In a normal uninhibited sample the band of PIOP becomes smaller over a period of a few minutes and the center of the ring fills in with PIOP to form a solid dot in the center of the reaction area. The non-magnetic beads themselves are preferably not readily visible in the system and do not participate in determining an end point for the assay. The end point of the test is established by the position and mobility of the PIOP present in the reagent formulation. Motion of the PIOP in the reaction area imparted by the rotating magnetic field is required to activate the platelets through contact with the solid phase agonist (i.e. the ligand) present on both the PIOP and non-magnetic beads. The aggregation of the two solid phases can occur through platelet adhesion to the solid phase and then platelet activation leading to platelet/platelet binding (platelet aggregation), particularly in the case of using a platelet ligand on both types of particles. In such a case, the detection of platelet/leukocyte interaction can be performed by inclusion of a leukocyte marker, such as a fluorescent marker, in the reagent mixture. If platelet/leukocyte interaction results from the assay, then the marker will be more prevalent in the aggregated particles than in the surrounding medium. If no platelet/leukocyte interaction occurs, the marker will not be present in the aggregated particles to any significant extent, compared to the surrounding medium. The level of interaction of platelets and leukocytes can be determined by quantitative measurement of the marker's presence in the aggregated particles. Aggregation does not occur in the absence of platelets or in the presence of an inhibitor.

Alternatively, when one type of particle bears the platelet ligand and the other type of particle bears the leukocyte ligand, the presence of platelet/leukocyte interaction can be observed either directly or indirectly. If the leukocyte ligand is bound to the magnetic or PIOP particles, the presence of the interaction of platelets and leukocytes can be directly observed, since collapse of the PIOP ring will not occur without such interaction. On the other hand, if the leukocyte ligand is bound to the non-magnetic particles, the collapse of the PIOP ring into the dot may still occur through platelet/platelet interaction of platelet ligand coated PIOP, albeit much more slowly. Definitive determination of platelet/leukocyte interaction in this embodiment would be best done through use of a marker, such as the fluorescent markers noted above.

In the assay of this embodiment of the present invention, once the bound ligand has interacted with the platelets and/or leukocytes, the free fibrinogen naturally in the sample interacts with the activated platelets, causing platelet/platelet aggregation. If the platelets and/or leukocytes are hyperactivated, such as in the case of a myocardial infarction or stroke victim, platelet/leukocyte interaction also occurs. As the platelets (with or without leukocytes) aggregate, this increases the effective mass of the aggregate around the PIOP, causing the heavier aggregates to migrate inward from the outer ring of particles toward the center of the rotating magnetic field. As the assay progresses, the ring eventually collapses into a circular dot, which continues to rotate about the center of the rotating field.

The end point of the assay can be monitored by using reflected infra red light similar to that of the TAS analyzer. This is possible because the area of the reaction chamber covered by the dark ring is much greater than that of the solid dot. The signal can provide both a qualitative YES/NO response and a quantitative response, as described above.

The difference in signal produced by a ring versus a dot can be enhanced if a small spot of reflective material covers the very center of the reaction area. In this situation the dark ring of PIOP will disappear behind the reflecting material, thereby increasing the signal. Alternately the end point of the assay could be monitored by a video or infra red camera. The output of the camera can be digitized and the image subsequently analyzed to determine the formation of ring and dot structures.

Figure 1A:
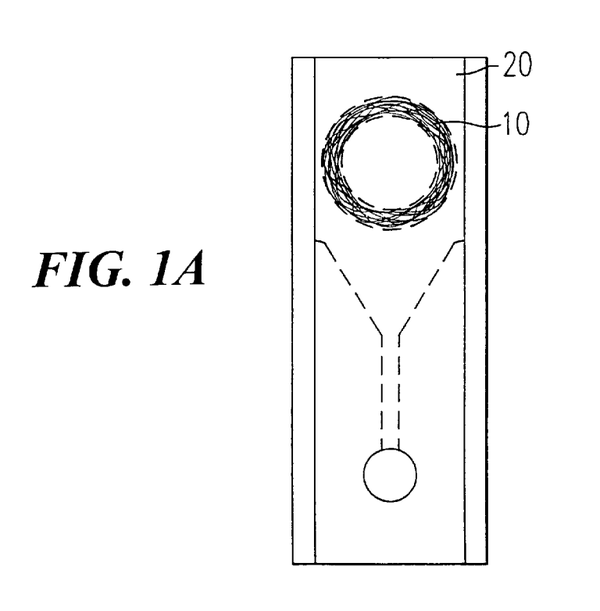
FIG. 1a is a representation of the PIOP ring formed during the assay of the present invention using a rotating magnetic field.

FIG. 1a provides a representation of the assay of the present invention in operation using a rotating magnetic field with an assay test card such as that from U.S. Pat. No. 5,110,727. In this Figure, the PIOP have been freed by the addition of the blood sample, resulting in the formation of a rotating ring (10) of PIOP within the reaction chamber (20).

Figure 1B:
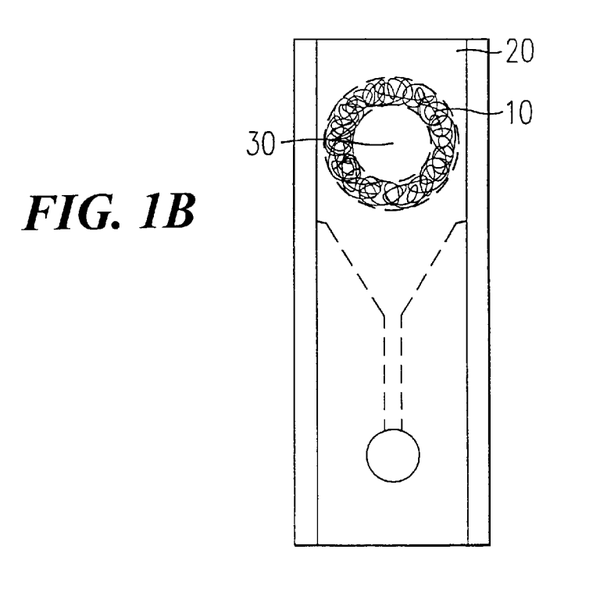
FIG. 1b is a representation of the PIOP ring formed during the assay as it begins to collapse toward the center point of the ring.
Figure 1C:
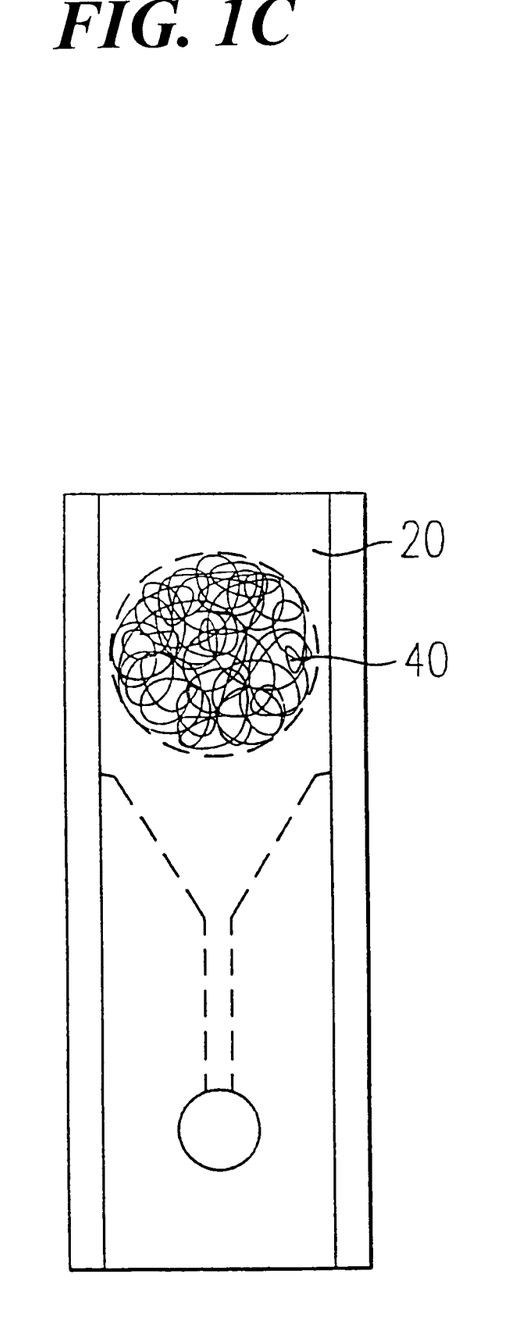
FIG. 1c is a representation of the disc or dot formed from complete collapse of the PIOP ring in the presence of a rotating magnetic field.

FIG. 1b shows the rotating ring (10) of PIOP has started to collapse toward the center point (30) representing the axis of the rotating field. FIG. 1c shows the endpoint of the assay in which the PIOP have completely collapsed into a dot structure (40). This endpoint is dramatic and readily detectable both instrumentally and visually. Visual detection provides a quick and easy method for obtaining the qualitative information discussed above, while instrumental detection using a system such as the TAS analyzer, provides the ability to analyze the signal obtained and provide quantitative measures of receptor blockage, preferably by comparison to a standard curve generated using samples of known platelet/leukocyte interaction levels.

When an oscillating magnetic field is used, the signal produced is analyzed in the same manner as in Oberhardt U.S. Pat. Nos. 5,110,727 and 4,849,340, by analysis of the decay curve produced by monitoring the oscillation of the particles.

Having generally described this invention, a further understanding can be obtained by reference to certain specific examples which are provided herein for purposes of illustration only, and are not intended to be limiting unless otherwise specified.

EXAMPLES

Preparation of vWf-coated PIOP. 10 g of Magnetite obtained from ISK Magnetics (Valparaiso, IN) was added to 90 mL of 50 mM Tris pH 7.4 in a sealed flask and purged with nitrogen for 5 minutes. The PIOP suspension was then homogenized by a model 700 PowerGen Homogenizer (Fisher Scientific) for 5 minutes at a setting of 6 using a 7 mm diameter rotor-Stator. A 0.7 mL aliquot of the homogenized PIOP was added to 0.3 mL of approximately 10 ug/mL vWf and allowed to incubate for 30 minutes at room temperature.

Preparation of vWf-coated polystyrene beads. Polystyrene beads (4 um) obtained from Polysciences Corporation (Warrington, Pa.) were washed three times with 0.2 mol/l carbonate buffer (pH 9.35) prior to use. vWf was diluted in 0.2 mol/l carbonate buffer (pH 9.35) to 2 U/mL (a unit of vWf is defined as the amount found in 1 mL of pooled normal plasma) and mixed with polystyrene beads pre-equilibrated in carbonate buffer prior to incubation overnight at 4° C.

Example 1

Figure 2:
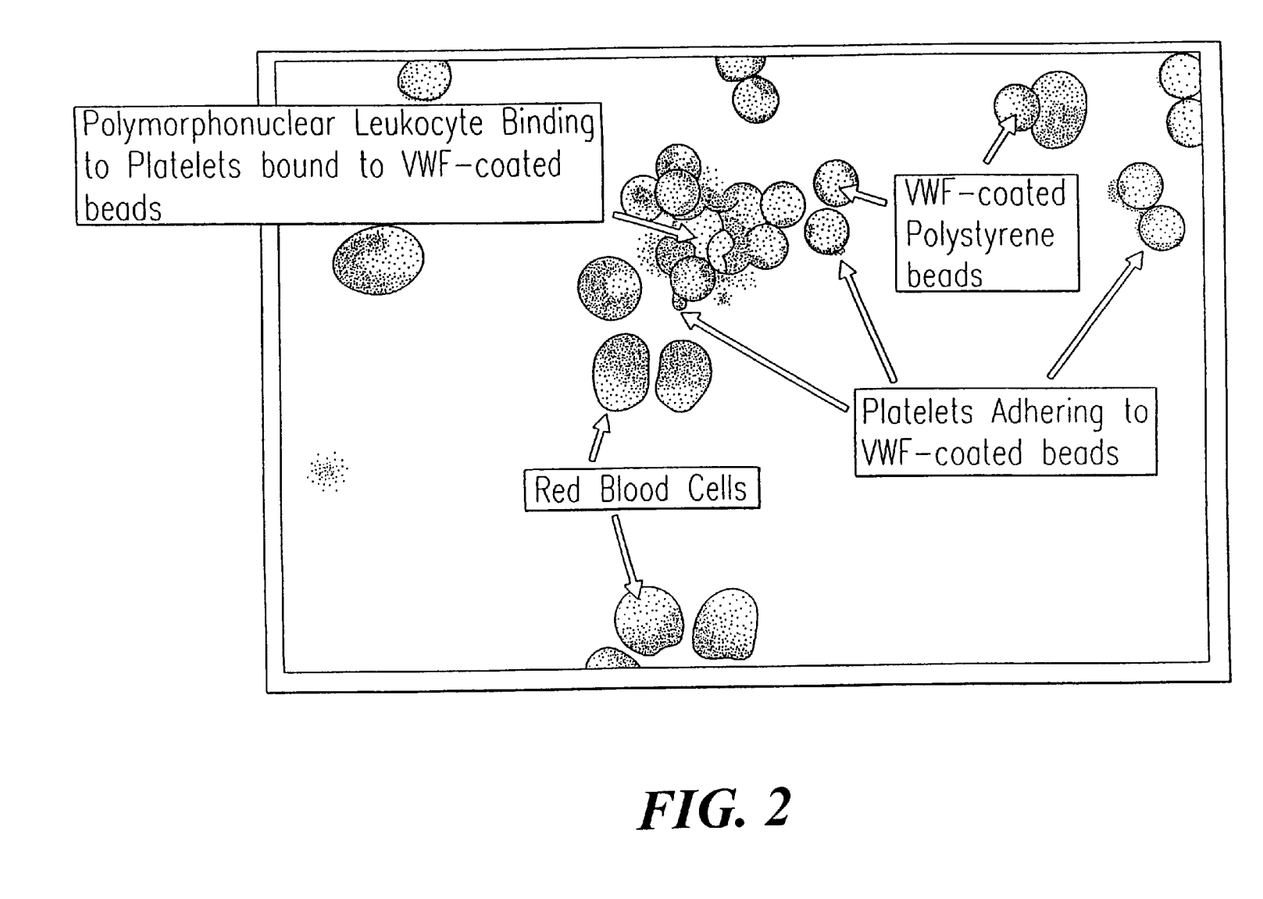
FIG. 2 is a photomicrograph showing the formation of a platelet/leukocyte/microparticle complex.

Whole blood from healthy volunteers collected into citrate as an anticoagulant was mixed with polystyrene microspheres coated with human von Willebrand factor. 100 $\mu$l of whole blood was added to 5 $\mu$l (approximately 5×10$^5$, 4.5 $\mu$m diameter) microspheres in microwells and shaken on a rotary shaker at 500 rpm for 1 to 10 minutes. Aliquots were removed from the microwells and examined by microscopy. The reaction was assessed using video microscopy, phase contrast microscopy and by differential staining on fixed smears. Leukocytes and platelets in complex were observed to be associated with the von Willebrand factor coated microspheres, only when the platelets displayed hyperactivity or when the platelets and/or leukocytes were subjected to mechanical stress such as repeated centrifugation (800×g, 10 minutes), or shearing by forcing the blood through a 21 gauge needle several times prior to testing. FIG. 2 shows an example of the platelet/leukocyte/vWf coated polystyrene bead complex, showing the polymorphonuclear leukocyte binding to platelets bound to vWf-coated beads.

Example 2

A differential cell count was performed on heparinized or citrated whole blood from healthy volunteers using an automated cell counter. 100 $\mu$l of whole blood was added to 5 $\mu$l (approximately 5×10$^5$, 4.5 $\mu$m diameter) von Willebrand factor coated microspheres in microwells and shaken on a rotary shaker at 500 rpm for 1 to 10 minutes. A second count was then performed on the reaction suspension. Taking into account the dilution effect of the bead reagent, the decrease in the number of leukocytes was determined by calculating the ratio between the post reaction counts and the pre-reaction counts and multiplying the result by 100 to obtain the percent decrease in leukocyte count. Concomitantly, uncoated nascent microspheres were mixed in a like manner with the anticoagulated whole blood and evaluated as described. The count data are tabulated in FIG. 3.

Leukocyte counts were seen to decrease after mixing the anticoagulated whole blood with the von Willebrand factor coated microspheres only when the platelets displayed hyperactivity or when the platelets and/or leukocytes were subjected to mechanical stress such as repeated centrifugation (800×g, 10 minutes), or shearing by forcing the blood through a 21 gauge needle several times prior to testing. In contrast, testing with uncoated microspheres showed no decrease in leukocyte counts. Phase contrast microscopy confirmed leukocyte/platelet complex association with the von Willebrand factor coated microspheres in aggregates and no association with the uncoated microspheres. The aggregates formed by the leukocytes, platelets and von Willebrand factor coated microspheres were noted to be too large to be counted as leukocytes, by the differential cell counter.

Example 3

Study subjects (n=3) destined for Coronary Artery Bypass Graft (CABG) surgery were tested prior to, and throughout the surgical procedure, using the method of the present invention. A differential cell count was performed on citrated whole blood at each time point (pre-surgery, on bypass, post-protamine, intensive care unit, 24 hours post-surgery) throughout the surgical procedure. In addition, 100 $\mu$l of citrated whole blood from each time point was added to microwells containing 5 $\mu$l (approximately 5×105, 4.5 $\mu$m diameter) von Willebrand factor coated microspheres. The microwells were shaken on a rotary shaker at 500 rpm for 1 to 10 minutes. A second differential cell count was performed on the blood from the microwells. Taking into account the dilution effect of the bead reagent, the decrease in the number of leukocytes was determined by calculating the ratio between the post reaction counts and the pre-reaction counts and multiplying the result by 100 to obtain the percent decrease in leukocyte count. All study subjects showed loss of leukocytes in the pre-surgical sample as determined by the differential cell counting technique. Microscopy confirmed platelet/leukocyte complex formation on the surface of the VWF coated microspheres. Platelet/leukocyte complex formation in the presence of the VWF coated microspheres was noted in the blood samples collected while the patients were on bypass, however platelet/leukocyte complex formation in the presence of the VWF coated microspheres was not seen in blood samples collected 24 hours post-surgery, in any of the study subjects.

Example 4

Whole blood from a healthy volunteer was drawn into a citrate vacutainer tube, an EDTA vacutainer tube and a heparin vacutainer tube. A drop of blood from each tube was added to the reaction well of three separate reaction cards containing a mixture of VWF-coated polystyrene beads and VWF-coated paramagnetic iron oxide particles (VWF-PIOP) and the suspension mixed vigorously for 5 minutes. Aliquots of whole blood (5 $\mu$l) were removed from each card for microscopic wet-mount observation (phase contrast) and stained smear (Hema-3 stain, Fisher Scientific) evaluation. Weak platelet adhesion to the VWF beads was noted with the EDTA blood, with the vast majority of platelets left unbound. Platelets did not associate with VWF-PIOP in the EDTA blood. Both the citrate blood and the heparin blood samples showed extensive binding of platelets to VWF beads with subsequent binding of VWF-PIOP to form large complexes. Few platelets were left unbound. Binding of leukocytes to (or within) these large VWF bead/platelet/VWF-PIOP complexes was not observed either by wet mount or stained smear. Leukocytes and platelets in complex were observed to be associated with the von Willebrand factor coated microspheres and VWF-PIOP in the citrate and heparin samples only when the platelets displayed hyperactivity or when the platelets and/or leukocytes were subjected to mechanical stress such as repeated centrifugation (800×g, 10 minutes). Mechanical stress did not augment platelet association with the VWF Beads or VWF-PIOP, nor did it promote leukocyte/platelet complex formation in the EDTA blood sample.

Preparation of test card—Into a test card, such as that in Oberhardt, U.S. Pat. No. 5,110,727, having a reaction chamber of approximately 30 $\mu$l, is placed a reagent composition containing the above noted magnetic and non-magnetic particles coated with vWf, in amounts such that the reagent composition comprises 1–2 mg of coated PIOP particles per ml and from 2×106 to 8×106 polystyrene particles per ml. Also placed into the reaction chamber is an amount of a leukocyte marker, such as FITC-labeled anti-CD45, sufficient to provide a detectable signal. Once the reaction chamber is filled, the sample is then frozen and lyophilized, as described for the preparation of test cards in the above noted Oberhardt patents.

However, the ratio of coated magnetic particles to coated non-magnetic particles is not limited and can be any ratio so long as there are sufficient magnetic particles to form the rotating ring and collapse to the disc or dot.

Platelet/Leukocyte Interaction Test. A disposable or test card containing the reagents described above is placed on a platform above a rotating magnet. Whole blood (or other blood-derived) sample is added to a well, which is pulled by capillary action into the reaction chamber. At that time the magnetic particles and non-magnetic particles are freed, with the magnetic particles forming a rotating ring around the central portion of the reaction chamber. As the reaction progressed, the inner edge of the rotating ring migrated toward the center, with the final endpoint providing a full collapse of the inner edge to the central point to form a disc or dot. The total time elapsed is approximately 1 to 20 minutes, typically in the 2–4 minute range.

When the above noted vWf coated PIOP and vWf coated polystyrene particles are used, the presence of platelet/leukocyte interaction is determined by detection of a leukocyte marker present in the original reagent formulation. Alternatively, if the PIOP are coated with a leukocyte ligand (instead of vWf) the occurrence of the platelet/leukocyte interaction is detected by collapse of the PIOP ring itself.

Obviously, numerous modifications and variations of the present invention are possible in light of the above teachings. It is therefore to be understood that within the scope of the appended claims, the invention may be practiced otherwise than as specifically described herein.

The present application is based on U.S. Provisional Application No. 60/165,462, filed Nov. 15, 1999, the entire contents of which are hereby incorporated by reference.

What is claimed is:

1. A platelet/leukocyte interaction assay method, comprising:

contacting a whole blood or blood-derived sample containing platelets and leukocytes with a platelet/leukocyte interaction assay reagent in the presence of an oscillating or rotating magnetic field, said platelet/leukocyte interaction assay reagent comprising a leukocyte marker compound and a mixture of magnetic and non-magnetic particles, wherein said magnetic particles have bound to an outer surface thereof an amount of a first ligand having an affinity for direct interaction with blood platelets and wherein said non-magnetic particles have bound to an outer surface thereof an amount of a second ligand having an affinity for direct interaction with blood platelets, wherein said first ligand and said second ligand can be the same or different; and monitoring movement of the magnetic particles in response to the oscillating or rotating magnetic field, to determine the presence or absence of platelet/leukocyte interaction function, a level of platelet/leukocyte interaction, or both, in the whole blood or blood-derived sample containing platelets and leukocytes as determined by comparing a level of leukocyte marker compound in an aggregate formed of said magnetic and non-magnetic particles to a level of leukocyte marker compound outside of said aggregate.

2. The method of claim 1, wherein said sample is whole blood.

3. The method of claim 1, wherein said first ligand is a member selected from the group consisting of von Willebrand factor, fibrinogen, fibronectin, Factor II, Factor IIa, Factor V, Factor Va, Factor VIII, Factor VIIIa, Factor IX, Factor IXa, Factor X, Factor Xa, Factor XI, Factor XIa, Factor XII, Factor XIIa, Factor XIII, Factor XIIIa, collagen, vitronectin, laminin, osteopontin, fibrillin, chondroitin sulfate, heparin sulfate, and active fragments thereof.

4. The method of claim 3, wherein said first ligand is von Willebrand factor or an active fragment thereof.

5. The method of claim 1, wherein said second ligand is a member selected from the group consisting of von Willebrand factor, fibrinogen, fibronectin, Factor II, Factor IIa, Factor V, Factor Va, Factor VIII, Factor VIIIa, Factor IX, Factor IXa, Factor X, Factor Xa, Factor XI, Factor XIa, Factor XII, Factor XIIa, Factor XIII, Factor XIIIa, collagen, vitronectin, laminin, osteopontin, fibrillin, chondroitin sulfate, heparin sulfate, and active fragments thereof.

6. The method of claim 5, wherein said second ligand is von Willebrand factor or an active fragment thereof.

7. The method of claim 1, wherein said first ligand and said second ligand are the same.

8. The method of claim 7, wherein said first ligand and said second ligand are each von Willebrand factor or an active fragment thereof.

9. The method of claim 1, wherein said first ligand and said second ligand are different from one another.

10. The method of claim 9, wherein one of said first ligand or said second ligand is von Willebrand factor or an active fragment thereof.

11. The method of claim 1, wherein said contacting occurs in the presence of a rotating magnetic field.

12. The method of claim 11, wherein said rotating magnetic field is rotating at a frequency of from 2000–2500 rpm.

13. A platelet/leukocyte interaction assay method, comprising:

contacting a whole blood or blood-derived sample containing platelets and leukocytes with a platelet/leukocyte interaction assay reagent in the presence of an oscillating or rotating magnetic field, said platelet/leukocyte interaction assay reagent comprising a mixture of magnetic and non-magnetic particles, wherein either said magnetic particles or said non-magnetic particles has bound to an outer surface thereof an amount of a first ligand having an affinity for direct interaction with blood platelets and the other of said magnetic particles or said non-magnetic particles has bound to an outer surface thereof an amount of a second ligand having an affinity for direct interaction with leukocytes; and detecting the presence or absence of platelet/leukocyte interaction function, a level of platelet/leukocyte interaction, or both, in the whole blood or blood-derived sample containing plateets and leukocytes.

14. The method of claim 13, wherein said sample is whole blood.

15. The method of claim 13, wherein said first ligand is a member selected from the group consisting of von Willebrand factor, fibrinogen, fibronectin, Factor II, Factor IIa, Factor V, Factor Va, Factor VIII, Factor VIIIa, Factor IX, Factor IXa, Factor X, Factor Xa, Factor XI, Factor XIa, Factor XII, Factor XIIa, Factor XIII, Factor XIIIa, collagen, vitronectin, laminin, osteopontin, fibrillin, chondroitin sulfate, heparin sulfate, and active fragments thereof.

16. The method of claim 15, wherein said first ligand is von Willebrand factor or an active fragment thereof.

17. The method of claim 13, wherein said second ligand is a member selected from the group consisting of leukocyte selective antibodies, VCAM-1, fibronectin, laminin, ICAM-1, ICAM-2, ICAM-3, collagen osteopontin, vWf, vitronectin, thrombospondin, mucosal addressin cell adhesion molecule 1 (MadCAM-1), P-selectin, L-selectin, and E-selectin.

18. The method of claim 13, wherein said first ligand is bound to said non-magnetic particles and said second ligand is bound to said magnetic particles.

19. The method of claim 13, wherein said first ligand is bound to said magnetic particles and said second ligand is bound to said non-magnetic particles.

20. The method of claim 19, wherein said platelet/leukocyte interaction reagent further comprises a leukocyte marker compound.

21. The method of claim 20, wherein said leukocyte marker compound is a fluorescent marker compound.

22. The method of claim 18, wherein said detecting is performed by monitoring movement of said magnetic particles in response to said oscillating or rotating magnetic field.

23. The method of claim 19, wherein said detecting is performed by monitoring movement of said magnetic particles in response to said oscillating or rotating magnetic field.

24. The method of claim 20, wherein said detecting is performed by detection or quantitation, or both, of differences in concentration of said leukocyte marker compound in said sample after coagulation of said sample.

25. The method of claim 13, wherein said contacting occurs in the presence of a rotating magnetic field.

26. The method of claim 25, wherein said rotating magnetic field is rotating at a frequency of from 2000–2500 rpm.

* * * * *